US00PP37177P2

(12) United States Plant Patent
Capo

(10) Patent No.: US PP37,177 P2
(45) Date of Patent: Dec. 23, 2025

(54) ***PETUNIA* PLANT NAMED 'KLEPH24833'**

(50) Latin Name: ***Petunia* x *atkinsiana* (syn. *P.* x *hybrida*)**
Varietal Denomination: KLEPH24833

(71) Applicant: KLEMM + SOHN GMBH & CO. KG, Stuttgart (DE)

(72) Inventor: Antonella Capo, Latina (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/269,809

(22) Filed: Jul. 15, 2025

(51) Int. Cl.
*A01H 6/82* (2018.01)
*A01H 5/02* (2018.01)

(52) U.S. Cl.
USPC ..... Plt./356.13

(58) Field of Classification Search
USPC ..... Plt./356.13
CPC ..... A01H 6/824; A01H 5/02
See application file for complete search history.

*Primary Examiner* — Keith O. Robinson
(74) *Attorney, Agent, or Firm* — Weatherly IP Solutions, LLC; Karen P. Bechtold; James M. Weatherly

(57) ABSTRACT

A new *Petunia* plant particularly distinguished by magenta flowers with a violet-colored eye and a semi-trailing plant habit, is disclosed.

1 Drawing Sheet

Genus and species: *Petunia* x *atkinsiana* (syn. *P.* x *hybrida*).

Variety denomination: 'KLEPH24833'.

BACKGROUND OF THE NEW PLANT

The present invention comprises a new and distinct variety of *Petunia*, botanically known as *Petunia* x *atkinsiana* (syn. *P.* x *hybrida*) and hereinafter referred to by the variety name 'KLEPH24833'. 'KLEPH24833' is a selection from a controlled cross between the proprietary female *Petunia* line 'PH-2019-9645' (unpatented) and the male *Petunia* line 'Capella Pink Lace' (unpatented).

In July of 2020 the proprietary female *Petunia* line 'PH-2019-9645' (unpatented) and the proprietary male *Petunia* line 'Capella Pink Lace' (unpatented) were cross pollinated in Latina, Italy and seeds were obtained. The seeds were sown and plants were grown for evaluation. A plant line was selected in April 2021 in Latina, Italy and named 'KLEPH24833'. In May 2021, 'KLEPH24833' was first vegetatively propagated by terminal tip cuttings and tissue culture in Latina, Italy. 'KLEPH24833' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Magenta flowers with a violet-colored eye; and
2. Semi-trailing plant habit.

DESCRIPTION OF THE PHOTOGRAPH

This new *Petunia* plant is illustrated by the accompanying photograph, which shows a close-up of the flower of the plant. The plant is about 20 weeks old in August 2024, grown outdoors in Stuttgart, Germany. The colors shown are as true as can be reasonably obtained by conventional photographic procedures.

DESCRIPTION OF THE NEW VARIETY

The following detailed descriptions set forth the distinctive characteristics of 'KLEPH24833'. The data which define these characteristics were collected from asexual reproductions carried out in Latina, Italy. Data was collected on thirteen-week-old plants grown indoors in Latina, Italy under greenhouse conditions in May 2025. Color references are to The R.H.S. Colour Chart of The Royal Horticultural Society of London (R.H.S.), 5$^{th}$ edition (2007).

Classification:
- *Family*.—Solanaceae.
- *Species*.—*Petunia* x *atkinsiana* (syn. *P.* x *hybrida*).
- *Common name*.—*Petunia*.
- *Variety*.—'KLEPH24833'.

Parentage:
- *Female parent*.—'PH-2019-9645' (unpatented).
- *Male parent*.—'Capella Pink Lace' (unpatented).

Plant:
- *Form and habit*.—Medium vigor, semi-trailing habit.
- *Height* (*from top of soil*).—20.0 cm.
- *Width* (*horizontal plant diameter*).—60.0 cm.
- *Propagation type*.—Vegetative by terminal tip cuttings and tissue culture.
- *Time to produce a finished flowering plant*.—About 12 weeks in winter under short day conditions, about 7 weeks in spring.
- *Time to initiate and develop roots*.—2 to 3 weeks.
- *Root description*.—Moderate density, moderate branching, white roots (RHS 155C).

Stems:
- *Average number* (*basal*).—7.
- *Length of basal branches* (*from the base of the stem to the tip*).—45.0 cm.
- *Internode length*.—1.5 cm.

*Diameter of branches* (*from midpoint*).—0.4 cm.
*Stem color*.—RHS 144A.
*Anthocyanin*.—Present, RHS N77A.
*Texture*.—Pubescent.

Leaves:
*Arrangement*.—Alternate along the stem and opposite under the inflorescence.
*Length*.—5.0 cm.
*Width*.—3.5 cm.
*Shape*.—Broadly elliptic to circular.
*Apex*.—Obtuse.
*Base*.—Attenuate.
*Margin*.—Entire.
*Immature leaf color*.—Upper surface: RHS 138A. Lower surface: RHS 138B.
*Mature leaf color*.—Upper surface: RHS 137B. Lower surface: RHS 138B.
*Texture*.—Upper surface: Pubescent. Lower surface: Pubescent.
*Venation pattern*.—Arcuate.
*Venation color*.—Upper surface: RHS 137B. Lower surface: RHS 144A.
*Petioles*.—Length: 0.6 cm. Diameter: 0.3 cm. Color: RHS 144B. Texture: Pubescent.

Flower bud:
*Shape*.—Irregularly oblong.
*Length*.—4.5 cm.
*Diameter*.—0.8 cm.
*Color at tight bud*.—RHS N77D.
*Texture*.—Pubescent.

Inflorescence:
*Blooming habit* (*flowering season*).—Continuously flowering during spring and summertime.
*Inflorescence type*.—Sympodial, with monochasial growth.
*Number of flowers per node*.—1.
*Lastingness of individual blooms on the plant*.—About 10 days.
*Fragrance*.—Absent.
*Flowers*.—Arrangement: Composed of 5 petals, fused at the base. Diameter (flower face): 5.5 cm. Depth (total length of flower): 5.7 cm. Throat/Funnel: Length: 2.8 cm. Diameter (at opening): 1.2 cm. Texture: Inner surface: Smooth. Outer surface: Pubescent. Color: Inner surface: RHS 76A. Outer surface: RHS 76B to RHS 76C with veins RHS N77A. Petals: Color, mature flower (fully opened): Upper surface: RHS N72C to RHS N72D and with RHS H74C veins. Lower surface: RHS 75B. Apex: Slightly cuspidate. Base: Fused. Shape: Funnelform. Margin: Entire. Strength of waviness: Medium Degree of lobation: Strong.
*Calyx arrangement*.—5 sepals fused at the base.
*Sepals*.—Color: Upper surface: RHS 137B. Lower surface: RHS 143C. Length: 1.6 cm. Width: 0.4 cm. Shape: Linear. Apex: Obtuse. Base: Attenuate. Margin: Entire. Texture: Upper surface: Pubescent. Lower surface: Pubescent.
*Pedicels*.—Color: RHS 144A. Length: 2.5 cm. Diameter: 0.15 cm. Texture: Pubescent.

Reproductive organs:
*Stamens*.—Quantity: 5. Shape: Needle with oblong head. Filament: Length: From 1.1 cm to 1.6 cm. Diameter: 0.01 cm. Color: RHS 193C. Anther: Shape: Oblong. Color: RHS N88D. Length: 0.2 cm. Diameter: 0.15 cm. Pollen: Color: RHS 92A. Amount: Moderate.
*Pistils*.—Quantity per flower: 1. Length: 2.2 cm. Stigma color: RHS 147B. Style color: RHS 147 D at the base and 79 A at distal portion, under the stigma.

Fruit and seed set: None observed.
Disease and pest/insect resistance: None observed.

COMPARISON WITH PARENTAL LINES AND KNOWN VARIETY

'KLEPH24833' is a distinct variety of *Petunia*. 'KLEPH24833' is distinguished from its parents as described in Tables 1 and 2:

TABLE 1

Comparison with Female Parent

| Characteristic | Subject Variety 'KLEPH24833' | Female parent 'PH-2019-9645' (unpatented) |
|---|---|---|
| Flower color | Magenta pink with dark eye | Magenta pink with cream throat |

TABLE 2

Comparison with Male Parent

| Characteristic | Subject Variety 'KLEPH24833' | Male Parent 'Capella Pink Lace' (unpatented) |
|---|---|---|
| Growth | Medium vigor semi trailing | Compact mounding |

'KLEPH24833' is most similar to the commercial *Petunia* plant named 'KLEPH22622' (unpatented). Differences between the two varieties are described in Table 3:

TABLE 3

Comparison with Similar Variety

| Characteristic | Subject Variety 'KLEPH24833' | Commercial line 'KLEPH22622' (unpatented) |
|---|---|---|
| Flower color and pattern | Magenta with a violet eye and no secondary color at the petal edge | Eye of the flower marked by dark veins and white petal edge |

I claim:

1. A new and distinct variety of *Petunia* plant named 'KLEPH24833' as shown and described herein.

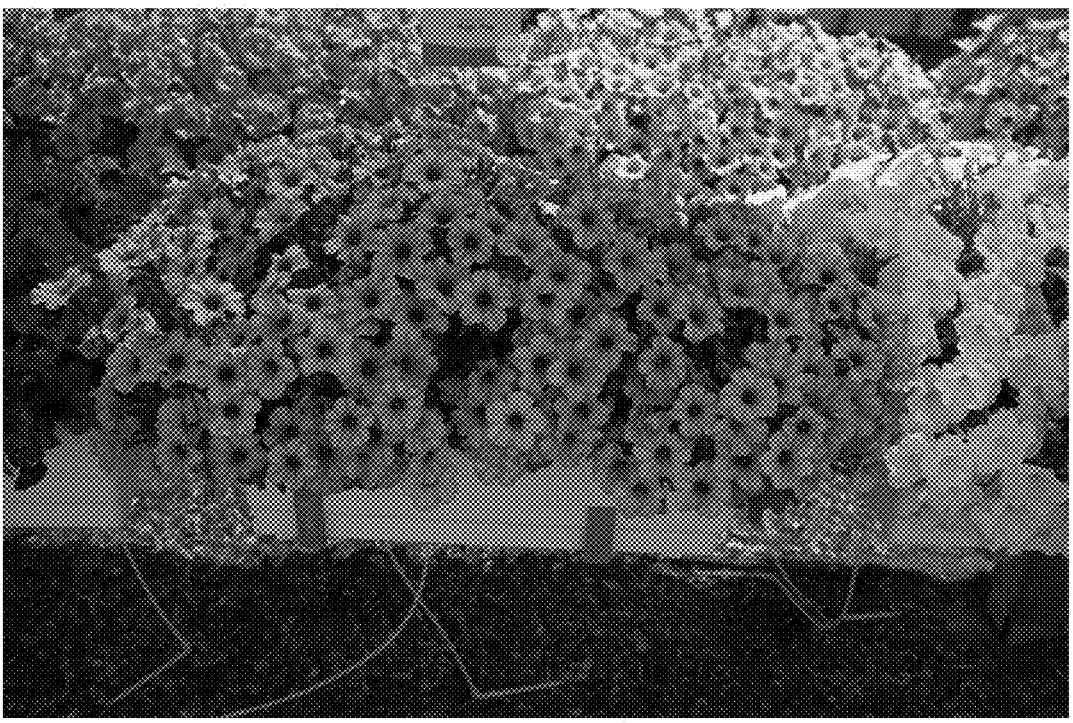

* * * * *